United States Patent [19]

Kawajiri et al.

[11] Patent Number: 5,177,260

[45] Date of Patent: Jan. 5, 1993

[54] METHOD FOR PRODUCTION OF ACRYLIC ACID

[75] Inventors: Tatsuya Kawajiri; Shinichi Uchida; Hideyuki Hironaka, all of Himeji, Japan

[73] Assignee: Nippon Shokubai Kagaku Kogyo Co., Ltd., Osaka, Japan

[21] Appl. No.: 608,832

[22] Filed: Nov. 5, 1990

[30] Foreign Application Priority Data

Nov. 6, 1989 [JP] Japan .................. 1-287518

[51] Int. Cl.$^5$ .................. C07C 51/16; C07C 51/235
[52] U.S. Cl. .................. 562/535
[58] Field of Search .................. 562/535

[56] References Cited

U.S. PATENT DOCUMENTS

| | | |
|---|---|---|
| 3,567,772 | 3/1971 | Yanagita et al. |
| 3,574,729 | 4/1971 | Gasson et al. |
| 3,773,692 | 11/1973 | Hensel et al. |
| 3,867,438 | 2/1975 | Hensel et al. |
| 3,954,855 | 5/1976 | Wada et al. |
| 4,039,582 | 8/1977 | Nasyrov et al. |
| 4,157,987 | 6/1979 | Dolhyj et al. |
| 4,297,247 | 10/1981 | Krabetz et al. |
| 4,333,858 | 6/1982 | Decker et al. |
| 4,359,407 | 11/1982 | Dolhyj et al. |
| 4,414,411 | 11/1983 | Decker et al. |
| 4,414,412 | 11/1983 | DeAlberti et al. |
| 4,595,778 | 6/1986 | Duembgen et al. |
| 4,621,155 | 11/1986 | Ueshima et al. |
| 4,892,856 | 1/1990 | Kawajiri et al. |

FOREIGN PATENT DOCUMENTS 1468005 3/1977 United Kingdom .

Primary Examiner—José G. Dees
Assistant Examiner—Joseph M. Conrad, III
Attorney, Agent, or Firm—Burns, Doane, Swecker & Mathis

[57] ABSTRACT

A method for the production of acrylic acid by the vapor-phase oxidation of acrolein with a molecular oxygen-containing gas in the presence of a catalyst formed of an oxide or a composite oxide of a metal element composition represented by the following formula I:

$$Mo_a V_b W_c Cu_d X_e Y_f \qquad (I)$$

wherein X is at least one element selected from the group consisting of Zr, Ti and Ce, Y is at least one element selected from the group consisting of Mg, Ca, Sr and Ba, and the subscripts a, b, c, d, e, and f are such that b=1 to 14, $0<c\leq12$, $0<d\leq6$, $0<e\leq10$, and f=0 to 3 where a is fixed at 12, $2.0<Cu+X\leq10.0$ and $0.25\leq Cu/X\leq6.0$.

12 Claims, No Drawings

METHOD FOR PRODUCTION OF ACRYLIC ACID

BACKGROUND OF THE INVENTION

1. Field of the Invention

This invention relates to a method for the production of acrylic acid. More particularly, it relates to a method for producing acrylic acid in a high yield with high productional efficiency and lasting stability by the vapor-phase catalytic oxidation of acrolein.

2. Description of the Prior Art

Heretofore, numerous patents have issued to inventions relating to catalysts for the production of acrylic acid from acrolein. In the catalysts covered by these inventions, the molybdenum-vanadium containing catalysts are predominant. As examples of the patents covering these molybdenum-vanadium containing catalysts, JP-B-44-26,287(1969), JP-B-47-8,360(1972), JP-B-53-43,917(1978), JP-B-57-54,172(1982), JP-B-48-16,493(1973), JP-A-50-97,592(1975), JP-A-51-70,718(1976), and JP-A-51-70,719(1976) may be cited.

Among these catalysts are included those whose yields of acrylic acid have reached considerably high levels from the industrial point of view. These catalysts of high yields have found actual utility in processes for the production of acrylic acid by direct oxidation of propylene. From the standpoint of the question as to whether or not these catalysts are capable of maintaining such yields of acrylic acid stably for a long time, however, none of the conventional molybdenum-vanadium containing catalysts are fully satisfactory. Concerning the service life of catalyst, there are published patents which cover catalysts confirmed to retain their performance stably for periods on the order of 4,000 hours. None of the conventional catalysts are fully satisfactory in terms of stability of catalyst performance after actual use in a commercial production over several years. The catalysts disclosed in the patents cited above are invariably short of being fully satisfactory in terms of yield and catalyst life. One of the probable reasons for their deficiency in performance is that, in the commercial application of these catalysts, the catalysts tend to undergo reduction because the reaction is carried out for a long time in the neighborhood of the theoretical oxygen demand for the sake of the oxidation of acrolein.

For the prevention of this decline of the catalytic activity, such measures as increasing the ratio of oxygen to acrolein and augmenting the amount of coexisting steam have been adopted to data. The measure resorting to the increase of the ratio of oxygen, however, is not desirable because the increase is subject to the imposition of an upper limit from the standpoint of avoiding a range of inflammability and the addition of oxygen and that of air inevitably entail complication and enlargement of the apparatus for production. Further, the increase of the oxygen content tends to induce an excessive reaction and results in lowering the selectivity of the conversion of acrolein to acrylic acid. In the case of the measure resorting to the increase of the amount of coexisting steam, although it is effective for the conventional catalytic system, the consumption of energy is large during the step for separation of acrylic acid and the cost incurred in the replenishment of steam with purified water cannot be ignored. Naturally, it is preferable to use a method or a catalyst which is capable of producing acrylic acid in a high yield with lasting stability while enabling the ratio of oxygen to acrolein to approximate the theoretical oxygen demand and allowing the amount of coexisting steam to be decreased to the fullest possible extent.

An object of this invention, therefore, is to provide a method for producing acrylic acid in a high yield by the vapor-phase catalytic oxidation of acrolein.

Another object of this invention is to provide a method for producing acrylic acid in a high yield with lasting stability by the vapor-phase catalytic oxidation of acrolein.

Still another object of this invention is to provide a catalyst to be used in the production of acrylic acid by the vapor-phase catalytic oxidation of acrolein, specifically an oxidation catalyst which enables acrylic acid to be produced in a high yield with lasting stability.

SUMMARY OF THE INVENTION

These objects are accomplished by a method for the production of acrylic acid by the vapor-phase oxidation of acrolein with a molecular oxygen-containing gas in the presence of a catalyst formed of an oxide or a composite oxide of a metallic element composition represented by the following formula I:

$$Mo_a V_b W_c Cu_d X_e Y_f \qquad (I)$$

wherein Mo is molybdenum, V is vanadium, W is tungsten, Cu is copper, X is at least one element selected from the group consisting of zirconium, titanium, and cerium, Y is at least one element selected from the group consisting of magnesium, calcium, strontium, and barium, and the subscripts a, b, c, d, e, and f are such that $b=1$ to 14, $0<c\leq 12$, $0<d\leq 6$, $0<e\leq 10$, and $f=0$ to 3 where a is fixed at 12, $2.0<Cu+X\leq 10.0$ and $0.25\leq Cu/X\leq 6.0$, and preferably prepared by using porous anatase type titanium dioxide possessing an average particle diameter in the range of 0.4 to 0.7 μm and a BET specific surface area in the range of 10 to 60 m²/g, zirconium oxide possessing an average particle diameter in the range of 0.01 to 1.0 μm and a BET specific surface area in the range of 5 to 150 m²/g, and cerium oxide possessing an average particle diameter in the range of 0.1 to 2.0 μm and a specific surface area in the range of 50 to 200 m²/g respectively as the raw materials for titanium, zirconium, and cerium.

In the present invention, owing to the use of a catalyst formed of an oxide or a composite oxide of a specific metal element composition, acrylic acid can be produced in a high yield with lasting stability. To be specific, the catalyst to be used in the present invention allows acrylic acid to be produced in a high yield from acrolein and this catalyst can be used for a long time without any discernible decline of activity.

EXPLANATION OF THE PREFERRED EMBODIMENT

Now, the present invention will be described in detail below.

The catalyst which is used in the present invention is an oxide or a composite oxide of a metal element composition represented by the aforementioned formula I. In the formula, a catalyst for oxidation of acrolein useful in industry is a composite oxide containing molybdenum and vanadium as main components as disclosed in the present invention. Thus, the molybdenum component (oxide) is apt to sublimate by action of steam, especially when steam exists in the reaction system and is apt to scatter from the catalytic substance, and as a result, activity of the catalyst decreases and selectivity to acrylic acid decreases. However, the existence of steam in the reaction system is effective in respect of the catalystic life. Further, if the amount of oxygen in the reaction system is low, it is apt to be reduced and the reduction reaction proceeds along with proceedings of the oxidation of acrolein and deterioration of the catalyst becomes remarkable.

We have studied in order to overcome such defect to find that the scattering of the molybdenum component and excess of reduction can be depressed and makes possible to produce acrylic acid for a long time by combination of copper component with zirconium and/or titanium and/or cerium and have completed the present invention. As mentioned above, the combination of copper with the X component is necessary, but it is not always previously combine the copper component with the X component, if the X component is an oxide having the above defined properties, it is especially effective to attain the above-mentioned object. If the X component is a compound of a form except the oxide, bond occurs between the X component and molybdenum or vanadium component, and oxidation action of molybdenum and vanadium which is a main component of the catalyst of the present invention is decreased, and as a result it is inconvenient because it is a reason for decrease of activity and selectively. For the X component, weak bond with active seed which is composed by molybdenum and vanadium is important. Further, if there is no X component, only the copper component cannot exhibit the sufficient effect and only the X component (although it contains tungsten) cannot attain the long life of the catalyst. Furthermore, if the X component is used as a compound except the oxide, it has found that the properties varies remarkably by slight difference of the method for the production, for example, by slight difference of calcination difference, so the catalyst cannot produced with good reproductivity.

Then about the relation of total of copper and the X component (X excluding oxygen), if Cu+X exceed 10.0, dilution effect appears and activity of the catalyst decreases, so it is not preferable. On the other hand, if it is less than 2.0, scattering of molybdenum and excess reduction proceed, so it is not preferable in respect of the attainment of long life which is one of the object of the present invention. About the definition of the ratio of the copper and X components, if the copper is too large out of the range of $0.25 \leq Cu/X \leq 6$ and the X component is too small, scattering of molybdenum and excess reduction cannot be surpressed. On the contrary, if the amount of the copper is too small and that of the X component is too large, the natural properties of the X component itself appears along with the effect of the X component, and selectivity to acrylic acid remarkably decreases. Therefore, good balance between the copper and X components, and scattering of the molybdenum component and excess reduction can be suppressed by the definition of such range, and reoxidation activity of the catalyst is exhibited and the activity and selectivity can be maintained even if low steam and low oxygen atmosphere in industrial scale for a long time. Further, addition of an alkaline earth element Y contributes of quality of acrylic acid. It has an effect for surpress the generation of a slight amount of the by-products.

In the aforementioned formula, the subscripts a, b, c, d, e, and f are such that b, c, d, e, and f are in the following ranges, b=1 to 14, preferably b=2 to 6, $0<c\leq12$, preferably c=0.3 to 6, $0<d\leq6$, preferably d=1 to 6, $0<e\leq10$, preferably e=0.5 to 8, and f=0 to 3, preferably f=0 to 2, where a=12. Further, total of Cu and X component is $2.0<Cu+X\leq10.0$, preferably $3\leq Cu+X\leq9$, and atomic ratio of Cu to X component is $0.25\leq Cu/X\leq6.0$, preferably $0.3\leq Cu/X\leq4$.

This invention does not discriminate the catalyst for use therein on account of the procedure to be employed for the preparation of the catalyst. The catalyst can be prepared by any of the known methods on the sole condition except that the produced catalyst possesses a metal element composition represented by the aforementioned formula I and an oxide having a specific physical properties is used as the X component.

The materials capable of forming the components of the catalyst, namely the precursors of these components, may be formed by any of the conventional method. For example, they may be converted into a slurry, dried, and then formed by the extrusion molding method or the compression molding method. Otherwise, the components of the catalyst may be deposited on an inactive porous carrier. Substances which are inactive and porous or capable of being pelletized into porous particles are invariably usable as the porous carrier. Typical examples of such substances are α-alumina, silicon carbide, pumice, silica, zirconium oxide, and titanium dioxide. Particularly, a carrier which possesses a surface area not exceeding 2 m$^2$/g, preferably falling in the range of 0.01 to 1.5 m$^2$/g and a porosity in the range of 10 to 65%, preferably 30 to 60%, and contains pores such that those having diameters of 1 to 1500 μm, preferably 5 to 500 μm account for a proportion exceeding 80%, preferably falling in the range of 90 to 100%, of the whole pores is advantageously used. The catalyst and the carrier therefor may be in the shape of spheres, cylinders, or hollow tubes.

Now, one example of the procedure for the preparation of the catalyst to be used in this invention will be described below.

First, ammonium molybdate, ammonium metavanadate, and optionally the nitrate of an alkaline earth metal (the element represented by Y in the aforementioned formula) are dissolved and mixed in water. The resultant mixed aqueous solution, aqueous solutions of ammonium paratungstate and copper nitrate added thereto and at least one oxide selected from the group consisting of zirconium oxide, titanium dioxide, and cerium oxide and added thereto are evaporated by heating to dryness. The dried mixture consequently obtained is pulverized. The produced powder is molded with an extrusion molding device in the shape of spheres having an average particle diameter in the range of 2 to 15 mm, preferably 3 to 10 mm, pellets, cylinders, rings, or honeycombs and calcined at a temperature in the range of 300° to 600° C., preferably 350° to 500° C., to produce a catalyst aimed at.

The additional use of an inactive porous carrier for the catalyst is accomplished by adding this carrier to the mixed aqueous solution subsequent to the addition of zirconium oxide, titanium dioxide, or cerium oxide, evaporating the resulting mixture to dryness in a ceramic evaporator thereby effecting deposition of the catalyst components on the carrier, and thereafter firing the dry mixture at a temperature in the range of 300° to 600° C., preferably 350° to 500° C.

The metallic compound to be used in the procedure for the preparation of the catalyst described above is not necessarily limited to an ammonium salt or a nitrate.

For example, molybdic acid, molybdenum trioxide, etc. are usable as a molybdenum compound and vanadium pentoxide, vanadyl oxalate, vanadyl sulfate, etc. are usable as a vanadium compound. Tungsten trioxide, tungstic acid, etc. are usable as a tungsten compound and organic acid salts, acetates, carbonates, chlorides, etc. of copper are usable as a copper compound. Further, alkaline earth metal compounds, carbonates, chlorides, sulfates, etc. are usable.

As titanium dioxide, it is necessary to use anatase type titanium dioxide which possesses an average particle diameter in the range of 0.4 to 0.7 μm, preferably 0.45 to 0.6 μm, and a BET (Brunauer-Emmett-Teller) specific surface area in the range of 10 to 60 m$^2$/g, preferably 15 to 40 m$^2$/g. The anatase titanium dioxide answering this description can be obtained by firing titanium dioxide at a temperature in the range of 600° to 900° C., preferably 650° to 850° C., for a period in the range of 2 to 12 hours, preferably 3 to 10 hours.

As zirconium oxide, it is necessary to use zirconium oxide which possesses an average particle diameter in the range of 0.01 to 1.0 μm, preferably 0.015 to 0.9 μm, and a BET specific surface area in the range of 5 to 150 m$^2$/g, preferably 8 to 69 m$^2$/g. The zirconium oxide answering this description is obtained by calcining such a zirconium compound as zirconyl nitrate, zirconyl carbonate, zirconyl sulfate, or zirconyl chloride at a temperature in the range of 600° to 900° C., preferably 650° to 850° C., for a period in the range of 2 to 12 hours, preferably 3 to 10 hours.

As cerium oxide, it is necessary to use cerium oxide which possesses an average particle diameter in the range of 0.1 to 2.0 μm, preferably 0.1 to 1.9 μm, and a BET specific surface area in the range of 50 to 200 m$^2$/g, preferably 60 to 180 m$^2$/g. The cerium oxide of this description is obtained by firing such a cerium compound as cerium carbonate, cerium nitrate, cerium sulfate, or cerium chloride at a temperature in the range of 300° to 600° C., preferably 320° to 580° C., for a period in the range of 1 to 12 hours, preferably 2 to 10 hours.

The method to be employed for the production of acrylic acid by the gaseous-phase catalytic oxidation of acrolein as contemplated by this invention is not particularly limited. This production can be attained by any of the known methods. For example, the production is effected by subjecting a mixed gas comprising 1 to 15% by volume, preferably 4 to 12 by volume, of acrolein, 0.5 to 25% by volume, preferably 2 to 20 by volume, of oxygen, 0 to 30% by volume, preferably 3 to 25 by volume, of steam, and 20 to 80% by volume, preferably 50 to 70 by volume, of an inert gas to a reaction at a space velocity in the range of 500 to 20,000 hr$^{-1}$, preferably 1,000 to 10,000 hr$^{-1}$, in the presence of the catalyst described above at a temperature in the range of 180° to 350° C., preferably 200° to 330° C., optionally under a vacuum and generally under a pressure in the range of from normal pressure to 10 atmospheres. As the feed gas, it is naturally permissible to use a raw gas composed of acrolein and oxygen or an inert gas, to use a formed gas containing acrolein resulting from direct oxidation of propylene in an unmodified form, or to use this formed gas as mixed with air, oxygen, and optionally further with steam. The byproducts mingling in the formed gas, i.e. oxidation products such as acrylic acid, acetaldehyde, and acetic acid, carbon oxides, and unaltered propylene and propane, have absolutely no adverse effect upon the catalyst to be used in the present invention.

The method of this invention can be carried out in a fixed bed system or a fluidized bed system.

Now, this invention will be described more specifically below with reference to working examples.

The conversion, selectivity, and per pass yield have been found in accordance with the following formulas.

| | |
|---|---|
| Conversion (mol %) = | (Number of mols of acrolein consumed in reaction/number of mols of acrolein supplied) × 100 |
| Selectivity (mol %) = | (Number of mols of produced acrylic acid/number of mols of acrolein consumed in reaction) × 100 |
| Per pass yield (%) | (Number of mols of produced acrylic acid/number of mols acrolein supplied) × 100 |

REFERENTIAL EXAMPLE 1

Porous anatase type titanium dioxide possessing an average particle diameter of 0.5 μm and a BET specific surface area of 22 m$^2$/g was obtained by calcining titanium hydroxide at 800° C. under a current of air for 4 hours and subjecting the calcined mass to a pulverizing treatment using a jet of air.

REFERENTIAL EXAMPLE 2

Zirconium oxide possessing an average particle diameter of 0.2 μm and a BET specific surface area of 25 m$^2$/g was obtained by calcining zirconyl nitrate at 750° C. in a current of air for 3 hours and subjecting the calcined mass to a pulverizing treatment using a jet of air.

REFERENTIAL EXAMPLE 3

Cerium oxide possessing an average particle diameter of 1.5 μm and a BET specific surface area of 120 m$^2$/g was obtained by calcining cerium carbonate in a current of air at 350° C. and subjecting the fired mass to a pulverizing treatment using a jet of air.

EXAMPLE 1

In 3,000 ml of water kept heated and stirred, 1,014 g of ammonium paramolybdate and 224 g of ammonium metavanadate were dissolved. Separately, in 6,000 ml of water kept heated and stirred, 231 g of copper nitrate and 323 g of ammonium paratungstate were dissolved. The two aqueous solutions were mixed and 118 g of the zirconium oxide obtained in Referential Example 2 was added to the resultant mixed aqueous solution. The produced mixture was concentrated by heating, then evaporated to dryness on a water bath, and further dried at 120° C.

The dried solid mass consequently obtained was pulverized to about 100 mesh, molded with an extrusion molding device in the shape of cylinders 5 mm in diameter and 6 mm in length, and heat treated in a current of air at 400° C. for 6 hours, to prepare a catalyst. The metal element composition of this catalyst except for oxygen was as follows.

$$Mo_{12}V_{14}W_{2.5}Cu_2Zr_2$$

A U-shaped tube of stainless steel 25 mm in diameter was packed with 1,000 ml of the catalyst obtained as described above and was immersed in a fused nitrate bath heated to 200° C. Into this U-shaped tube, a mixed gas resulting from the vapor-phase catalytic oxidation of industrial-grade propylene in the presence of a molybdenum-bismuth type catalyst and comprising 5.0% by volume of acrolein, 1.2% by volume of unreacted propylene plus by-produced organic compound, 4.0% by volume of oxygen, 16.0% by volume of steam, and 73.8% by volume of nitrogen-containing inert gas was fed for reaction at a space velocity (SV) of 3,000 hr$^{-1}$. This reaction was continued for 4,000 hours, 8,000 hours, and 16,000 hours. At the end of each of these intervals, the catalyst was tested for performance. The results are shown in Table 1. The temperature of the nitrate bath was varied with the reaction time.

EXAMPLE 2

In 2,500 ml of water kept heated and stirred, 338 g of ammonium paramolybdate and 75 g of ammonium metavanadate were dissolved. Separately, in 2,000 ml of water kept heated, 78 g of copper nitrate, 108 g of ammonium paratungstate, and 6.8 g of strontium nitrate were dissolved. The two aqueous solutions thus obtained were mixed and 76.5 g of the titanium dioxide obtained in Referential Example 1 was added to the produced mixed aqueous solution.

In a ceramic evaporator held on a water bath, the mixed solution obtained as described above and 1,000 ml of a granular carrier of $\alpha$-alumina measuring 3 to 5 mm in diameter, possessing a surface area of not more than 1 m$^2$/g and a porosity of 40–50% and, containing pores such that those of not more than 500 $\mu$m in diameter account for 90% of the whole pores were stirred and evaporated to dryness to effect deposition of the catalyst components on a carrier. The produced mixture was heat treated in a curent of air at 400° C. for 6 hours, to prepare a catalyst. The metallic element composition of this catalyst except for oxygen was as follows.

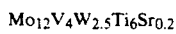

$Mo_{12}V_4W_{2.5}Ti_6Sr_{0.2}$

This catalyst was tested for performance by following the procedure of Example 1. The results are shown in Table 1. The initial temperature of the nitrate bath was 240° C.

EXAMPLE 3

A catalyst was prepared by following the procedure of Example 2, except that 51 g of the titanium dioxide obtained in Referential Example 1 and 54.9 g of the cerium oxide obtained in Referential Example 3 were used in the place of 76.5 g of titanium dioxide and 20.8 g of barium nitrate was used in the place of 6.8 g of strontium nitrate. This catalyst was tested for performance in the same manner as in Example 1. The results are shown in Table 1.

EXAMPLE 4 AND 5

Catalysts of metallic element compositions shown in Table 1 were prepared and tested for performance by following the procedure of Example 1. The results are shown in Table 1.

EXAMPLES 6 AND 7

Catalysts of metallic element compositions shown in Table 1 were prepared and tested for performance by following the procedure of Example 1. The results are shown in Table 1.

EXAMPLES 8 AND 9

The catalyst of Example 1 was tested for performance by following the procedure of Example 1, except that the space velocity was changed to 4,000 hr$^{-1}$ and 5,000 hr$^{-5}$. The results are shown in Table 1.

CONTROL 1

A catalyst was prepared by following the procedure of Example 1, except that the addition of zirconium oxide was omitted. This catalyst was tested in the same manner as in Example 1. The results are shown in Table 1.

It is understood from the results of Table 1 that the catalyst not containing the X component suffers the activity thereof to degrade conspicuously with the elapse of the reaction time.

EXAMPLES 10 TO 13

Catalysts of metal element compositions indicated in Table 1 were prepared by following the procedure of Example 2, except that commercially available silica-alumina carriers possessing specific surface areas not exceeding 2 m$^2$/g and a porosity in the range of 10 to 65% and containing pores such that those of 1 to 1,500 $\mu$m in diameter account for not less than 80% of the whole pores were used instead. These catalysts were tested for performance in the same manner as in Example 1. The results are shown in Table 1.

EXAMPLES 14 TO 16

Catalysts of metallic element compositions indicated in Table 1 were obtained by causing a mixed catalyst solution obtained in the same manner as in Example 2 to be deposited on a carrier of silicon carbide particles 3 to 5 mm in diameter and heat treating the resultant composite at 400° C. for 6 hours. These catalysts were tested for performance in the same manner as in Example 1. The results are shown in Table 1.

EXAMPLES 17 TO 20

Catalysts of metallic element compositions indicated in Table 1 were prepared by following the procedure of Example 1, except that the dried solid mass was compaction molded in the shape of rings 6 mm in outside diameter, 3 mm in inside diameter, and 6 mm in length instead of being extrusion molded. These catalysts were tested for performance in the same manner as in Example 1. The results are shown in Table 1.

EXAMPLES 21 TO 23

In Example 16, an amount of copper was changed to 3.0 and an amount of cerium of x component was changed to 0.5 (Example 21), and in Example 22, an amount of copper was changed to 1.0 to obtain a catalyst having the composition ratio excluding oxygen. These catalysts were tested for performance in the same manner as in Example 1. The results are shown in Table 1.

CONTROLS 2 TO 5

Catalysts of Controls 3-6 were obtained by preparing using the starting compounds in Example 1 so as to be the same catalytic composition as the composition shown in Table 1. These catalysts were tested for performance in the same manner as in Example 1. The results are shown in Table 1.

EXAMPLE 23

The catalyst of Example 2 was tested for performance by following the procedure of Example 2, except that a mixed gas composed of 8% by volume of acrolein, 4% by volume of oxygen, and the balance to make up 100% by volume of nitrogen was used as the feed gas for the reaction. The reaction, at the outset thereof, showed an acrolein conversion of 99.0 mol % and an acrylic acid per pass yield of 96.0 mol % at a fuxed nitrate bath temperature of 245° C. The reaction, after 8,000 hours' continued operation, showed an acrolein conversion of 98.5 mol % and an acrylic acid per pass yield of 95.5 mol % at a reaction temperature of 250° C.

From the results, it is confirmed that the catalyst of the present invention is effectively usable even in a reaction which is performed at a low oxygen concentration and a low steam concentration.

TABLE 1

| | Catalyst composition | | | | | | Temperature of used nitrate bath (°C.) | Reaction time (hrs) | Conversion of acrolein (mol %) | Perpass yield of acrylic acid (mol %) | Selectivity to acrylic acid (mol %) | Cu + X | Cu/ X |
|---|---|---|---|---|---|---|---|---|---|---|---|---|---|
| | Mo | V | W | Cu | X | Y | | | | | | | |
| Example | | | | | | | | | | | | | |
| 1 | 12 | 4 | 2.5 | 2 | Zr 2 | — | 200 | initial | 99.2 | 94.0 | 94.8 | 4 | 1 |
| | | | | | | | 205 | 4000 | 99.1 | 94.2 | 95.1 | | |
| | | | | | | | 205 | 8000 | 99.0 | 94.5 | 95.5 | | |
| | | | | | | | 207 | 16000 | 99.1 | 94.4 | 95.3 | | |
| 2 | 12 | 4 | 2.5 | 2 | Ti 6 | Sr 0.2 | 240 | initial | 98.9 | 97.6 | 98.7 | 8 | 0.33 |
| | | | | | | | 245 | 4000 | 98.6 | 97.4 | 98.8 | | |
| | | | | | | | 245 | 8000 | 98.5 | 97.2 | 98.7 | | |
| | | | | | | | 247 | 16000 | 98.6 | 97.2 | 98.6 | | |
| 3 | 12 | 4 | 2.5 | 2 | Ti 4, Ce 2 | Ba 0.5 | 240 | initial | 98.5 | 95.3 | 96.8 | 8 | 0.33 |
| | | | | | | | 245 | 4000 | 98.7 | 95.4 | 96.7 | | |
| | | | | | | | 245 | 8000 | 98.5 | 95.3 | 96.8 | | |
| | | | | | | | 247 | 16000 | 98.5 | 95.2 | 96.7 | | |
| 4 | 12 | 4 | 2.5 | 2 | Zr 2 | Mg 0.7 | 200 | initial | 98.7 | 93.4 | 94.6 | 4 | 1 |
| | | | | | | | 205 | 4000 | 98.5 | 93.1 | 94.5 | | |
| 5 | 12 | 4 | 2.5 | 2 | Zr 2 | Ca 1 | 200 | initial | 98.2 | 93.4 | 95.1 | 4 | 1 |
| | | | | | | | 205 | 4000 | 98.0 | 93.4 | 95.3 | | |
| 6 | 12 | 6 | 1 | 6 | Ti 2 | — | 255 | initial | 98.7 | 94.9 | 96.1 | 8 | 3 |
| | | | | | | | 255 | 4000 | 98.5 | 94.4 | 95.8 | | |
| 7 | 12 | 2.5 | 3 | 2.5 | Zr 4, Ce 2 | — | 245 | initial | 99.6 | 97.5 | 97.9 | 8.5 | 0.42 |
| | | | | | | | 250 | 4000 | 99.5 | 97.5 | 98.0 | | |
| 8 | 12 | 4 | 2.5 | 2 | Zr 2 | — | 210 | initial | 99.5 | 94.7 | 95.2 | 4 | 1 |
| | | | | | | | 215 | 4000 | 99.3 | 94.4 | 95.1 | | |
| 9 | 12 | 4 | 2.5 | 2 | Zr 2 | — | 220 | initial | 99.1 | 94.6 | 95.5 | 4 | 1 |
| | | | | | | | 225 | 4000 | 98.7 | 94.4 | 95.6 | | |
| Control 1 | 12 | 4 | 2.5 | 2 | — | — | 200 | initial | 98.7 | 93.5 | 94.7 | | |
| | | | | | | | 205 | 4000 | 98.2 | 92.9 | 94.6 | | |
| | | | | | | | 210 | 8000 | 96.5 | 91.2 | 94.5 | | |
| | | | | | | | 220 | 16000 | 94.0 | 88.5 | 94.2 | | |
| Example | | | | | | | | | | | | | |
| 10 | 12 | 4 | 6 | 2 | Ti 3, Ce 3 | Ca 0.5 | 240 | initial | 98.8 | 94.1 | 95.2 | 8 | 0.33 |
| | | | | | | | 245 | 4000 | 98.7 | 94.0 | 95.2 | | |
| 11 | 12 | 4 | 10 | 2 | Ti 2, Ce 2 | Mg 0.5 | 220 | initial | 98.2 | 93.1 | 94.8 | 8 | 0.33 |
| | | | | | | | 225 | 4000 | 98.5 | 93.5 | 94.9 | | |
| 12 | 12 | 2.5 | 0.5 | 2.5 | Zr 3, Ce 3 | | 245 | initial | 98.8 | 94.8 | 96.0 | 8.5 | 0.42 |
| | | | | | | | 250 | 4000 | 99.2 | 95.4 | 96.2 | | |
| 13 | 12 | 2.5 | 10 | 2 | Zr 4, Ce 2 | | 240 | initial | 98.3 | 93.9 | 95.5 | 8 | 0.33 |
| | | | | | | | 245 | 4000 | 98.7 | 93.9 | 95.1 | | |
| 14 | 12 | 6 | 0.5 | 4 | Ti 2 | | 255 | initial | 98.5 | 94.1 | 95.5 | 6 | 2 |
| | | | | | | | 260 | 4000 | 98.6 | 93.9 | 95.2 | | |
| 15 | 12 | 6 | 6 | 4 | Ti 1, Zr 1 | | 250 | initial | 99.0 | 93.9 | 94.8 | 6 | 2 |
| | | | | | | | 255 | 4000 | 99.2 | 94.1 | 94.9 | | |
| 16 | 12 | 4 | 2 | 4 | Ce 1 | Sr 0.2, Mg 0.3 | 245 | initial | 99.5 | 94.5 | 95.0 | 5 | 4 |
| | | | | | | | 250 | 4000 | 99.6 | 94.5 | 94.9 | | |
| 17 | 12 | 4 | 0.5 | 2 | Ti 1, Zr 2 | Ba 1 | 220 | initial | 99.7 | 94.9 | 95.2 | 5 | 0.67 |
| | | | | | | | 225 | 4000 | 99.6 | 94.6 | 95.0 | | |
| 18 | 12 | 4 | 2 | 2 | Ti 1, Zr 2 | | 210 | initial | 99.5 | 95.2 | 95.7 | 5 | 0.67 |
| | | | | | | | 215 | 4000 | 99.6 | 95.6 | 96.0 | | |
| 19 | 12 | 4 | 2 | 2 | Ti 3, Zr 3, Ce 2 | | 210 | initial | 99.2 | 95.0 | 95.8 | 10 | 0.25 |
| | | | | | | | 215 | 4000 | 99.3 | 95.2 | 95.9 | | |
| 20 | 12 | 6 | 2 | 2 | Ti 1, Zr 3, Ce 1 | Sr 0.1, Ca .04 | 205 | initial | 98.7 | 94.6 | 95.8 | 7 | 0.4 |
| | | | | | | | 210 | 4000 | 99.3 | 95.3 | 96.0 | | |
| 21 | 12 | 4 | 2 | 3 | Ce 0.5 | Sr 0.2, Mg 0.3 | 245 | initial | 98.9 | 94.2 | 95.3 | 3.5 | 6 |
| | | | | | | | 250 | 4000 | 99.2 | 94.6 | 95.4 | | |
| 22 | 12 | 4 | 2 | 1 | Ce 1.0 | Sr 0.2, Mg 0.3 | 250 | initial | 99.0 | 94.1 | 95.0 | 2 | 1 |
| | | | | | | | 255 | 4000 | 98.8 | 93.7 | 94.8 | | |
| Control | | | | | | | | | | | | | |
| 2 | 12 | 4 | 2.5 | 1 | Zr 0.5 | — | 205 | initial | 98.7 | 93.9 | 95.1 | 1.5 | 2 |
| | | | | | | | 215 | 4000 | 96.9 | 91.9 | 94.8 | | |
| 3 | 12 | 4 | 2.5 | 5 | 6.0 | — | 210 | initial | 96.3 | 91.2 | 94.7 | 11 | 0.83 |
| 4 | 12 | 4 | 2.5 | 5 | 0.6 | — | 210 | initial | 93.5 | 88.5 | 94.6 | 5.6 | 8.33 |
| | | | | | | | 220 | 4000 | 89.0 | 84.0 | 94.4 | | |
| 5 | 12 | 4 | 2.5 | 1.0 | 5 | — | 200 | initial | 94.2 | 85.5 | 90.8 | 6 | 0.20 |

What is claimed is:

1. A method for the production of acrylic acid by the vapor-phase oxidation of acrolein with a molecular oxygen-containing gas in the presence of a catalyst formed of an oxide or a composite oxide of a metal element composition represented by the following formula I:

$$Mo_a V_b W_c Cu_d X_e Y_f \quad (I)$$

wherein Mo is molybdenum, V is vanadium, W is tungsten, Cu is copper, X is at least one element selected from the group consisting of zirconium and titanium, Y is at least one element selected from the group consisting of magnesium, calcium, strontium, and barium, and the subscripts a, b, c, d, e, and f are such that b=1 to 14, $0<c\leq12$, $0<d\leq6$, $0<e\leq10$, and f=0 to 3 when a is 12; $2.0<Cu+X\leq10.0$ and $0.25\leq Cu/X\leq6.0$.

2. A method according to claim 1, wherein said reaction is carried out at a temperature in the range of 180° to 350° C. at a spatial velocity in the range of 500 to 20,000 $hr^{-1}$.

3. A method according to claim 1, wherein said catalyst is prepared by the steps of combining porous anatase titanium dioxide possessing an average particle diameter in the range of 0.4 to 0.7 micron and a BET specific surface area in the range of 10 to 60 $m^2/g$, and a zirconium oxide possessing an average particle diameter in the range of 0.01 to 1.0 micron and a BET specific surface area in the range of 5 to 150 $m^2/g$, converting said combined materials into a slurry, drying the resultant slurry, and forming same into a catalyst material.

4. The method of claim 3, wherein said titanium dioxide possesses an average particle diameter in the range of 0.45 to 0.6 micron and a BET specific surface area in the range of 15 to 40 $m^2/g$, and a zirconium oxide having an average particle diameter in the range of 0.015 to 0.9 micron and a BET specific surface area in the range of 8 to 69 $m^2/g$.

5. A method according to claim 1, wherein the subscripts a, b, c, d, e, and f are such that b is in the range of 2 to 6, c in the range of 0.3 to 6, d in the range of 1 to 6, e in the range of 0.5 to 8, and f in the range of 0 to 2, where a is fixed at 12, $3\leq Cu+X\leq9$ and $0.3\leq Cu/X\leq4$.

6. The method of claim 1, wherein said catalyst is prepared by depositing on an inactive porous carrier a porous anatase titanium dioxide possessing an average particle diameter in the range of 0.4 to 0.7 micron and a BET surface area in the range of 10 to 60 $m^2/g$ and a zirconium oxide possessing an average particle diameter in the range of 0.01 to 1.0 micron and a BET surface area in the range of 5 to 150 $m^2/g$.

7. The method of claim 6, wherein said inactive porous carrier is selected from the group consisting at alpha-alumina, silicon carbide, pumice, silica, zirconium oxide and titanium oxide.

8. The method of claim 1, wherein said oxidation is effected in the presence of steam.

9. The method of claim 8, wherein said oxidation is effected in the presence of an inert gas.

10. The method of claim 8, wherein said oxidation is effected using as a feed gas containing acrolein which is obtained by direct oxidation of propylene.

11. The method of claim 1, wherein said oxidation is effected using a feed gas containing acrolein which is obtained by the direct oxidation of propylene.

12. The method of claim 11, wherein said direct oxidation of propylene is effected in the presence of air, oxygen and steam.

* * * * *